US012726597B2

(12) United States Patent
Chen et al.

(10) Patent No.: US 12,726,597 B2
(45) Date of Patent: Sep. 1, 2026

(54) MONITORING VIDEO GENERATION

(71) Applicant: Siemens Shanghai Medical Equipment Ltd., Shanghai (CN)

(72) Inventors: Kai Chen, Shanghai (CN); Yi Tian, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 0 days.

(21) Appl. No.: 19/108,831

(22) PCT Filed: Aug. 3, 2023

(86) PCT No.: PCT/CN2023/111078
§ 371 (c)(1),
(2) Date: Mar. 5, 2025

(87) PCT Pub. No.: WO2024/051413
PCT Pub. Date: Mar. 14, 2024

(65) Prior Publication Data

US 2026/0082020 A1 Mar. 19, 2026

(30) Foreign Application Priority Data

Sep. 8, 2022 (CN) ........................ 202211095722.0

(51) Int. Cl.
*H04N 7/18* (2006.01)
*A61B 6/00* (2006.01)
(Continued)

(52) U.S. Cl.
CPC ............ *H04N 7/183* (2013.01); *A61B 6/032* (2013.01); *A61B 6/0407* (2013.01);
(Continued)

(58) Field of Classification Search
CPC .......... H04N 7/18; H04N 7/183; G06T 7/246; G06T 7/73; G06T 2207/10016;
(Continued)

(56) References Cited

U.S. PATENT DOCUMENTS 10,242,266 B2 * 3/2019 Jones ...................... G06N 3/08
10,726,264 B2 * 7/2020 Sawhney ................. G06T 7/20
(Continued)

FOREIGN PATENT DOCUMENTS

CN 103610470 A 3/2014
CN 111918023 A 11/2020
(Continued)

OTHER PUBLICATIONS

Abdul Rajjak Shaikh Shakil et al: "Recent Advances in Object Detection and Tracking for High Resolution Video: Overview and State-of-the-Art", 2019 5th International Conference on Computing, Communication, Control and Automation (ICCUBEA), IEEE; Sep. 19, 2019 (Sep. 19, 2019), pp. 1-9; XP033786255; DOI: 10.1109/ICCUBEA47591.2019.9128812; 2019.
(Continued)

*Primary Examiner* — Trang U Tran
(74) *Attorney, Agent, or Firm* — Banner & Witcoff, Ltd.

(57) ABSTRACT

A monitoring video generation method applicable to a CT machine, including: acquiring a plurality of primary videos including a monitored target, determining a keyframe according to a region in an initial frame of each primary video surrounding the monitored target, and determining a bounding box surrounding the monitored target in the keyframe; determining, for each primary video, a bounding box surrounding the monitored target in each subsequent frame; and selecting, for each frame moment from the frames of the plurality of primary videos, a frame in which the region of the monitored target within the bounding box has a largest
(Continued)

S10
Acquire a plurality of primary videos including the monitored target

S20
Determine a keyframe according to a region in an initial frame of each of the primary videos surrounding the monitored target, and determining a bounding box surrounding the monitored target in the keyframe S30
Determine, for each of the primary videos, a bounding box surrounding the monitored target in each subsequent frame S40
Select, for each frame moment from the frames of the plurality of primary videos, a frame in which the region of the monitored target within the bounding box has a largest area as the keyframe, and generate a monitoring video in real time according to a part of each selected keyframe located within the bounding box area as the keyframe, and generating a monitoring video in real time according to a part of each selected keyframe located within the bounding box.

7 Claims, 2 Drawing Sheets

(51) Int. Cl.
*A61B 6/03* (2006.01)
*A61B 6/04* (2006.01)
*G06T 7/246* (2017.01)
*G06T 7/73* (2017.01)
*G06V 20/40* (2022.01)
*G06V 20/52* (2022.01)

(52) U.S. Cl.
CPC ............ *A61B 6/4435* (2013.01); *G06T 7/246* (2017.01); *G06T 7/73* (2017.01); *G06V 20/46* (2022.01); *G06V 20/52* (2022.01); *G06T 2207/10016* (2013.01); *G06T 2207/20104* (2013.01); *G06T 2207/30004* (2013.01); *G06V 2201/03* (2022.01)

(58) Field of Classification Search
CPC ........... G06T 2207/20104; G06T 2207/30004; G06V 20/52; G06V 20/46; G06V 2201/03; A61B 6/032; A61B 6/0407; A61B 6/4435
USPC .......................................................... 348/143
See application file for complete search history.

(56) References Cited

U.S. PATENT DOCUMENTS 10,861,302 B2 * 12/2020 Savvides ................ G06N 20/00
10,873,697 B1 12/2020 Jain et al.
11,288,835 B2 * 3/2022 Ning ......................... G06T 7/73
11,494,935 B2 * 11/2022 Lee ........................... G06T 7/73
2006/0257048 A1 * 11/2006 Lin ........................ G06V 20/40 382/276
2019/0130191 A1 * 5/2019 Zhou ...................... G06V 20/52
2023/0005154 A1 1/2023 Garcia I Tormo et al.

FOREIGN PATENT DOCUMENTS

CN 112509000 A 3/2021
CN 113840159 A 12/2021
WO 2021110613 A1 6/2021

OTHER PUBLICATIONS

Nov. 6, 2023 (PCT) International Search Report and Written Opinion—App. PCT/CN2023/111078.

* cited by examiner

S10
Acquire a plurality of primary videos including the monitored target

S20
Determine a keyframe according to a region in an initial frame of each of the primary videos surrounding the monitored target, and determining a bounding box surrounding the monitored target in the keyframe S30
Determine, for each of the primary videos, a bounding box surrounding the monitored target in each subsequent frame

S40
Select, for each frame moment from the frames of the plurality of primary videos, a frame in which the region of the monitored target within the bounding box has a largest area as the keyframe, and generate a monitoring video in real time according to a part of each selected keyframe located within the bounding box

FIG. 1

S10
Acquire a plurality of primary videos including the monitored target

S50
Splice and/or stack the plurality of primary videos to form a secondary video composed of keyframes at all frame moments S60
Determine a bounding box in each of the keyframes of the secondary video to surround the monitored target S70
Generate and display a monitoring video in real time according to a part of each of the keyframes of the secondary video located within the bounding box

FIG. 2

MONITORING VIDEO GENERATION

TECHNICAL FIELD

The present disclosure relates to a monitoring video generation method and a monitoring video generation system configured to perform a monitoring video generation method.

BACKGROUND

During the movement of a patient into a computed tomography (CT) machine through a patient table, an operator observes, through the CT machine or a plurality of cameras in a scanning room, a status/action of the patient from all angles, which overcomes blind spots caused by the room layout and the patient orientation, thereby ensuring better patient care and patient safety during the entire CT examination.

In an existing method, a camera stream is displayed on a dedicated monitoring screen, and a video corresponding to each camera is played separately in a specific region of the monitoring screen. The operator needs to frequently switch the sight among the plurality of videos on the monitoring screen to capture a desired image, which easily leads to the loss of focus and visual fatigue.

SUMMARY

The present disclosure is intended to provide a monitoring video generation method, which can facilitate observation of a patient from a plurality of angles in a monitoring video.

The present disclosure is further intended to provide a monitoring video generation system, which can facilitate observation of a patient from a plurality of angles in a monitoring video.

The present disclosure provides a monitoring video generation method applicable to a CT machine. A monitored target is located on a patient table of the CT machine. The patient table of the CT machine is movable relative to a gantry of the CT machine in an extending direction. The monitoring video generation method includes: acquiring a plurality of primary videos including the monitored target, where fields of view of the plurality of primary videos are fixed relative to a position of the gantry of the CT machine; determining a keyframe according to a region in an initial frame of each of the primary videos surrounding a monitored target, and determining a bounding box surrounding the monitored target in the keyframe; determining, for each of the primary videos, a bounding box surrounding the monitored target in each subsequent frame; and selecting, for each frame moment from the frames of the plurality of primary videos, a frame in which the region of the monitored target within the bounding box has a largest area as the keyframe, and generating a monitoring video in real time according to a part of each selected keyframe located within the bounding box.

According to the monitoring video generation method provided in the present disclosure, a monitoring video may be generated in real time according to the primary videos of a plurality of cameras, which can facilitate observation of a patient from a plurality of angles in the monitoring video, thereby helping reduce the loss of focus and visual fatigue as a result of an operator frequently switching the sight among a plurality of videos on a monitoring screen.

In an exemplary implementation of the monitoring video generation method, the step of determining the keyframe according to the region in the initial frame of each of the primary videos surrounding the monitored target specifically includes: determining the region in the initial frame of each of the primary videos surrounding the monitored target through an automatic detection algorithm or manual selection, and selecting a frame in the initial frames in which the region surrounding the monitored target has a largest area as the keyframe.

In another exemplary implementation of the monitoring video generation method, the step of determining, for each of the primary videos, the bounding box surrounding the monitored target in each subsequent frame specifically includes: determining, for each of the primary videos, the bounding box surrounding the monitored target in each subsequent frame by using an automatic detection algorithm, a coordinate conversion algorithm, or an optical flow method.

In still another exemplary implementation of the monitoring video generation method, the step of determining the bounding box by using the coordinate conversion algorithm specifically includes: mapping, through a coordinate conversion algorithm, coordinates of a bounding box in a keyframe at a previous frame moment to a coordinate system where the gantry of the CT machine is located, calculating, according to a physical movement vector of the patient table of the CT machine relative to the gantry of the CT machine between two frames, a position of a bounding box in a frame at a next frame moment of the same primary video in the coordinate system where the gantry of the CT machine is located, then mapping the coordinates to a frame at a next frame moment of each of the primary videos according to coordinate correspondences between cameras that acquire the primary videos and between the cameras and the gantry, and determining a bounding box surrounding the monitored target after coordinate update in the frame at the next frame moment of each of the primary videos. Through the coordinate conversion, the coordinates of the bounding box in each subsequent frame may be calculated, which helps save calculation resources, thereby improving the real-time performance of the monitoring video.

In yet another exemplary implementation of the monitoring video generation method, the step of determining the bounding box by using the optical flow method specifically includes: calculating coordinates of a bounding box in a frame at a next frame moment of the same primary video through the optical flow method by using coordinates of a bounding box in a keyframe at a previous frame moment as a reference, then mapping, through coordinate conversion, the calculated coordinates of the bounding box in the frame at the next frame moment to a coordinate system where the gantry of the CT machine gantry is located, mapping the coordinates to a frame at a next frame moment of each of the primary videos according to coordinate correspondences between cameras that acquire the primary videos and between the cameras and the gantry, and determining a bounding box surrounding the monitored target after coordinate update in the frame at the next frame moment of each of the primary videos. In this way, the consumption of calculation resources is reduced.

The present disclosure further provides a monitoring video generation method. A monitored target is located on a patient table of a CT machine. The patient table of the CT machine is movable relative to a gantry of the CT machine in an extending direction. The monitoring video generation method includes: acquiring a plurality of primary videos including the monitored target, where fields of view of the plurality of primary videos are fixed relative to a position of the gantry of the CT machine; splicing and/or stacking the plurality of primary videos to form a secondary video composed of keyframes at all frame moments; determining a bounding box in each of the keyframes of the secondary video to surround the monitored target; and generating a monitoring video in real time according to a part of each of the keyframes of the secondary video located within the bounding box.

According to the monitoring video generation method provided in the present disclosure, a monitoring video may be generated in real time according to the primary videos of a plurality of cameras, which can facilitate observation of a patient from a plurality of angles in the monitoring video, thereby helping reduce the loss of focus and visual fatigue as a result of an operator frequently switching the sight among a plurality of videos on a monitoring screen.

In an exemplary implementation of the monitoring video generation method, the step of determining the bounding box in each of the keyframes of the secondary video to surround the monitored target specifically includes: determining the bounding box in each of the keyframes of the secondary video by using an automatic detection algorithm to surround the monitored target. In this way, automatic operation can be achieved, thereby reducing the labor consumption.

In another exemplary implementation of the monitoring video generation method, the step of determining the bounding box in each of the keyframes of the secondary video to surround the monitored target specifically includes: determining a bounding box in an initial keyframe through an automatic detection algorithm or manual selection to surround the monitored target, and determining a bounding box in each subsequent keyframe by using a coordinate conversion algorithm according to the bounding box determined in the initial keyframe. The coordinate conversion algorithm includes: calculating a movement vector from coordinates of the bounding box in the keyframe at a previous frame moment to coordinates of the bounding box in the keyframe at a next frame moment according to a physical movement vector of the patient table of the CT machine relative to the gantry of the CT machine between two frame moments, and calculating the coordinates of the bounding box in the keyframe at the next frame moment according to the coordinates of the bounding box in the keyframe at the previous frame moment and the coordinate movement vector. Through the coordinate conversion, the coordinates of the bounding box in each subsequent keyframe may be calculated, which helps save calculation resources, thereby improving the real-time performance of the monitoring video.

In another exemplary implementation of the monitoring video generation method, the step of determining the bounding box in each of the keyframes of the secondary video to surround the monitored target specifically includes: determining a bounding box in an initial keyframe through an automatic detection algorithm or manual selection to surround the monitored target, and determining a bounding box in each subsequent keyframe by using an optical flow method according to the bounding box determined in the initial keyframe. In this way, the consumption of calculation resources is reduced.

The present disclosure further provides a monitoring video generation system, including a computer-readable storage medium and a processor. The computer-readable storage medium stores code. When the processor executes the code, the monitoring video generation system performs the above monitoring video generation method. According to the monitoring video generation system, a monitoring video may be generated in real time according to the primary videos of a plurality of cameras, which can facilitate observation of a patient from a plurality of angles in the monitoring video, thereby helping reduce the loss of focus and visual fatigue as a result of an operator frequently switching the sight among a plurality of videos on a monitoring screen.

In an exemplary implementation of the monitoring video generation system, the monitoring video generation system further includes a display. The display has a display window, and the display window is configured to display a monitoring video generated in real time. The display displays the monitoring video generated in real time in a minimap mode or a Picture-in-Picture mode.

In another exemplary implementation of the monitoring video generation system, in the minimap mode, the display window is composed of a main window and a minimap window. The minimap window is configured to display a keyframe at each frame moment. The main window is configured to display a part of each keyframe located within a bounding box. A rectangular box exists on each keyframe displayed in the minimap window to indicate a position of the monitored target in each keyframe. In this way, the region of real interest is zoomed in in the main window while retaining an original image in the minimap window to provide position information.

In still another exemplary implementation of the monitoring video generation system, the display window in the Picture-in-Picture mode is composed of a main window and a child window. One of the main window and the child window is configured to display the monitoring video generated in real time, and the other is configured to display a primary video including the monitored target from a camera. Contents displayed in the main window and the child window are switched by clicking/tapping the child window. In this way, two different videos may be viewed simultaneously.

BRIEF DESCRIPTION OF DRAWINGS

The following drawings are merely exemplary descriptions and explanations and do not limit the scope of the present disclosure.

FIG. 1 is a schematic flowchart of an exemplary implementation of a monitoring video generation method.

FIG. 2 is a schematic flowchart of another exemplary implementation of the monitoring video generation method.

REFERENCE NUMERALS

Figure 3:
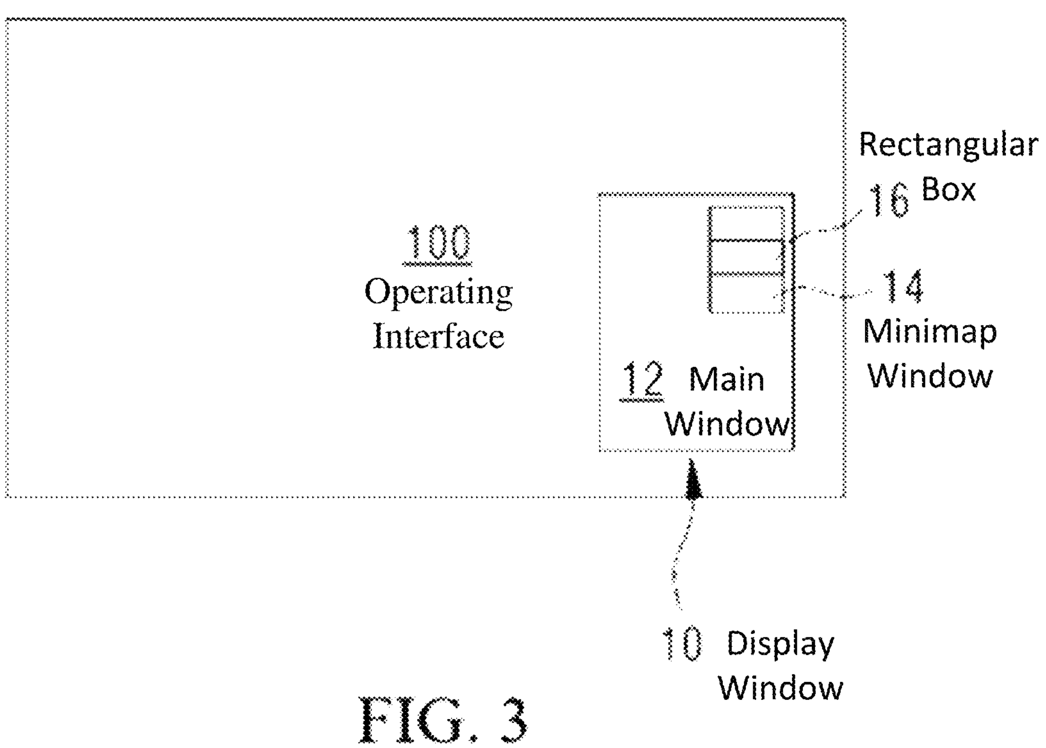
FIG. 3 is a schematic diagram describing a minimap mode.

100 Operating interface
10 Display window
12 Main window
14 Minimap window
16 Rectangular box
18 Child window

DETAILED DESCRIPTION

For a clearer understanding of the technical features, objectives, and effects of the present disclosure, specific implementations of the present disclosure are described with reference to the drawings. The same labels in the figures represent components with the same structure or similar structures but the same function.

Herein, "exemplary" means "being used as an instance, example, or description," and any illustration or implementation described as "exemplary" herein should not be interpreted as a more preferred or advantageous technical solution.

FIG. 1 is a schematic flowchart of an exemplary implementation of a monitoring video generation method. The monitoring video generation method is applicable to a CT machine. The CT machine is also referred to as a computed X-ray tomographic unit. During movement of a patient into a CT machine through a patient table, an operator observes, through the CT machine or a plurality of cameras in a scanning room, a status/action of the patient from all angles, which overcomes blind spots caused by the room layout and the patient orientation, thereby ensuring better patient care and patient safety during the entire CT examination.

The CT machine includes a display with a display window. A monitored target is located on a patient table of the CT machine. The patient table of the CT machine is movable relative to a gantry of the CT machine in an extending direction. Referring to FIG. 1, the monitoring video generation method includes the following steps:

Step S10: Acquire a plurality of primary videos including the monitored target (such as a patient), where fields of view of the plurality of primary videos are fixed relative to a position of the gantry of the CT machine.

Step S20: Determine a keyframe according to a region in an initial frame of each of the primary videos surrounding the monitored target, and determining a bounding box surrounding the monitored target in the keyframe. The "bounding box surrounding the monitored target" therein is explained as a "bounding box surrounding a region where the monitored target is displayed."

In an exemplary implementation, the keyframe may be determined through manual selection from the plurality of primary videos acquired in step S10, which specifically includes: comparing areas of the monitored target in the initial frames, selecting an initial frame in which the monitored target has a largest area as the keyframe, and drawing a bounding box on the keyframe, where the bounding box needs to surround the monitored target.

In another exemplary implementation, the keyframe may be determined through an automatic detection algorithm from the plurality of primary videos acquired in step S10, which specifically includes: inputting the initial frames of the acquired primary videos into the automatic detection algorithm, and executing the algorithm to automatically select an initial frame in which the monitored target has a largest area as the keyframe and to obtain coordinates of the bounding box on the keyframe. In this case, the bounding box is invisible.

Figure 4:
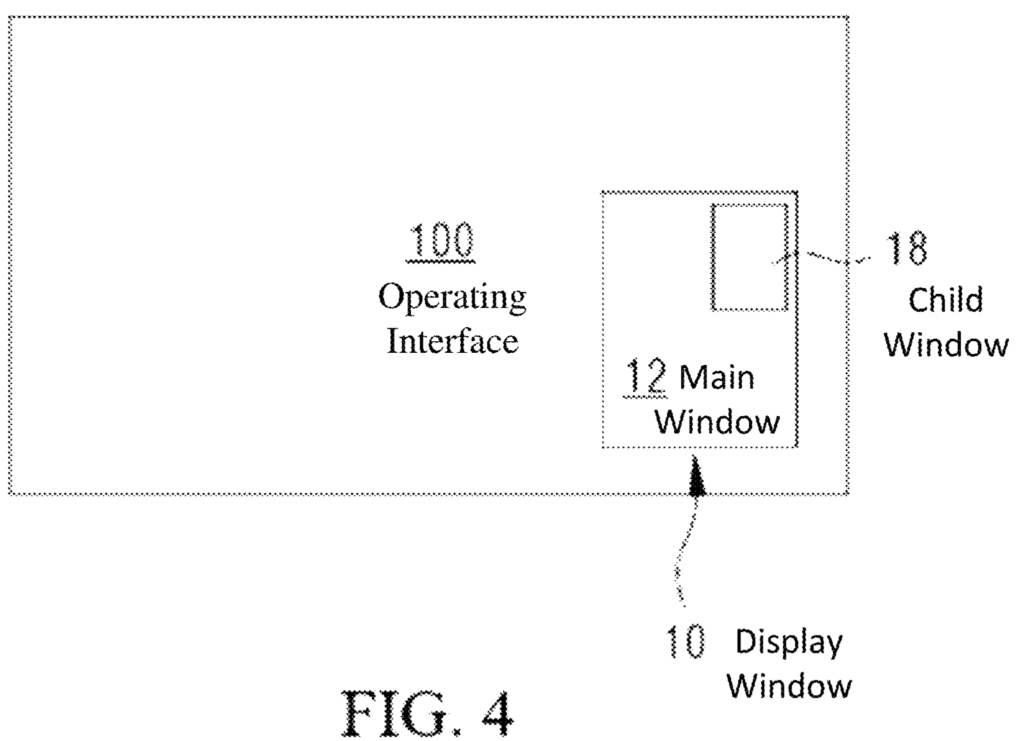
FIG. 4 is a schematic diagram describing a Picture-in-Picture mode.

As a frame of the monitoring video, the acquired keyframe is displayed in real time on a display window. As shown in FIG. 3 and FIG. 4, the CT machine includes a display with a display window 10. The display has an operating interface 100 configured to display CT scan results. The display window 10 configured to display the monitoring video generated in real time is arranged at a corner of the operating interface 100. The monitoring video generated in real time is displayed in a minimap mode or a Picture-in-Picture mode, for example.

In an exemplary implementation, the monitoring video generated in real time may be displayed in the minimap mode, as shown in FIG. 3. In the minimap mode, the display window 10 is composed of a main window 12 and a minimap window 14. The minimap window 14 is located at a corner of the main window 12 and is configured to display the keyframe. The main window 12 is configured to display the monitored targets within the bounding box of the keyframe. A rectangular box 16 exists on the keyframe displayed in the minimap window 14 to indicate a position of the monitored target in the keyframe.

In another exemplary implementation, the monitoring video generated in real time may be displayed in the Picture-in-Picture mode, as shown in FIG. 4. In the Picture-in-Picture mode, the display window 10 is composed of a main window 12 and a child window 18. The child window 18 is located at a corner of the main window 12. One of the main window 12 and the child window 18 is configured to display the monitoring video generated in real time, and the other is configured to display a primary video including the monitored target from a camera. Contents displayed in the main window 12 and the child window 18 are switched by clicking/tapping the child window 18. In this way, two different videos may be viewed simultaneously.

Step S30: Determine, for each of the primary videos, a bounding box surrounding the monitored target in each subsequent frame.

The step of determining, for each of the primary videos, the bounding box surrounding the monitored target in each subsequent frame specifically includes: determining the bounding box surrounding the monitored target in each subsequent frame by using an automatic detection algorithm, a coordinate conversion algorithm, or an optical flow method.

In an exemplary implementation, the step of determining the bounding box surrounding the monitored target in each subsequent frame by using the automatic detection algorithm specifically includes: detecting a frame of each inputted primary video at each moment, and acquiring, for each frame, the bounding box surrounding the monitored target.

In another exemplary implementation of the monitoring video generation method, the step of determining the bounding box surrounding the monitored target in each subsequent frame by using the coordinate conversion algorithm specifically includes: mapping, through a coordinate conversion algorithm, coordinates of a bounding box in a keyframe at a previous frame moment to a coordinate system where the gantry of the CT machine is located, calculating, according to a physical movement vector of the patient table of the CT machine relative to the gantry of the CT machine between two frames, a position of a bounding box in a frame at a next frame moment of the same primary video in the coordinate system where the gantry of the CT machine is located, then mapping the coordinates to a frame at a next frame moment of each of the primary videos according to coordinate correspondences between cameras that acquire the primary videos and between the cameras and the gantry, and determining a bounding box surrounding the monitored target after coordinate update in the frame at the next frame moment of each of the primary videos. Through the coordinate conversion, the coordinates of the bounding box in each next frame may be calculated, which helps save calculation resources, thereby improving the real-time performance of the monitoring video. A person skilled in the art knows that conversion among coordinates in each frame, camera coordinates, and gantry coordinates may be performed after calibrating internal and external parameters.

In still another exemplary implementation of the monitoring video generation method, the step of determining the bounding box surrounding the monitored target in the frame at each next frame moment by using the optical flow method specifically includes: calculating coordinates of a bounding box in a frame at a next frame moment of the same primary video through the optical flow method by using coordinates of a bounding box in a keyframe at a previous frame moment as a reference, then mapping, through coordinate conversion, the calculated coordinates of the bounding box in the frame at the next frame moment to a coordinate system where the gantry of the CT machine gantry is located, mapping the coordinates to a frame at a next frame moment of each of the primary videos according to coordinate correspondences between cameras that acquire the primary videos and between the cameras and the gantry, and determining a bounding box surrounding the monitored target after coordinate update in the frame at the next frame moment of each of the primary videos. In this way, the consumption of calculation resources is reduced.

Step S40: Select, for each frame moment from the frames of the plurality of primary videos, a frame in which the region of the monitored target within the bounding box has a largest area as the keyframe, and generate a monitoring video in real time according to a part of each selected keyframe located within the bounding box. For example, the monitoring video is displayed in the display window 10. The monitoring video generated in real time is composed of the keyframes at all frame moments. Therefore, a display mode of the monitoring video is the display mode of the keyframes. Details are not described.

According to the monitoring video generation method provided in the present disclosure, a monitoring video may be generated in real time according to the primary videos of a plurality of cameras, which can facilitate observation of a patient from a plurality of angles in the monitoring video, thereby helping reduce the loss of focus and visual fatigue as a result of an operator frequently switching the sight among a plurality of videos on a monitoring screen.

In addition, by arranging the display window 10 on the operating interface 100 of the display of the CT machine and displaying the monitoring video on the display window 10, no additional display screen is required, which can avoid the loss of focus and visual fatigue as a result of an operator switching the sight by a long distance between the operating interface 100 and the monitoring screen.

FIG. 2 is a schematic flowchart of another exemplary implementation of the monitoring video generation method. Referring to FIG. 2, the monitoring video generation method includes the following steps:

Step S10: Acquire a plurality of primary videos including the monitored target, where fields of view of the plurality of primary videos are fixed relative to a position of the gantry of the CT machine.

Step S50: Splice and/or stack the plurality of primary videos to form a secondary video composed of keyframes at all frame moments. The splicing and/or stacking of the primary videos is implemented by using commonly used methods.

Step S60: Determine a bounding box in each of the keyframes of the secondary video to surround the monitored target.

In an exemplary implementation, the monitored target is detected in each of the keyframes of the secondary video by using an automatic detection algorithm, and the bounding box is determined to surround the monitored target. In this way, automatic operation can be achieved, thereby reducing the labor consumption.

In another exemplary implementation, the monitored target is detected in an initial keyframe of the secondary video by using the automatic detection algorithm and the bounding box is determined to surround the monitored target, or the monitored target is manually selected and the bounding box is manually drawn to surround the monitored target. Then, the bounding box is determined in each subsequent frame according to the bounding box determined in the initial keyframe by using the coordinate conversion algorithm or the optical flow method.

The coordinate conversion algorithm specifically includes: calculating a movement vector from coordinates of the bounding box in the keyframe at a previous frame moment to coordinates of the bounding box in the keyframe at a next frame moment according to a physical movement vector of the patient table of the CT machine relative to the gantry of the CT machine between two frame moments, and calculating the coordinates of the bounding box in the keyframe at the next frame moment according to the coordinates of the bounding box in the keyframe at the previous frame moment and the coordinate movement vector. Through the coordinate conversion, the coordinates of the bounding box in each next keyframe may be calculated, which helps save calculation resources and generate the monitoring video in real time.

The optical flow specifically includes: calculating an optical flow between the keyframe at a previous frame moment and the keyframe at a next frame moment by using coordinates of the bounding box in the keyframe at the previous frame moment as a reference, and applying the optical flow to the coordinates of the bounding box in the keyframe at the previous frame moment to calculate coordinates of the bounding box in the keyframe at the next frame moment. In this way, there is no need to frequently read system information, which helps reduce the consumption of calculation resources.

Step S70: Generate and display a monitoring video in real time according to a part of each of the keyframes of the secondary video located within the bounding box. The display mode may be a minimap mode or a Picture-in-Picture mode. Details are not described herein.

According to the monitoring video generation method provided in the present disclosure, a monitoring video may be generated in real time according to the primary videos of a plurality of cameras, which can facilitate observation of a patient from a plurality of angles in the monitoring video, thereby helping reduce the loss of focus and visual fatigue as a result of an operator frequently switching the sight among a plurality of videos on a monitoring screen.

The present disclosure further provides a monitoring video generation system for a CT machine, including a computer-readable storage medium, a processor, and a display. The computer-readable storage medium stores code. When the processor executes the code, the monitoring video generation system performs the above monitoring video generation method. The display has an operating interface 100. A display window 10 is arranged on the operating interface 100. The display window 10 is configured to display a monitoring video generated in real time. By displaying the monitoring video generated in real time through the display window 10, no additional display screen is required.

The display displays the generated monitoring video in a minimap mode or a Picture-in-Picture mode in real time.

In the minimap mode, the display window 10 is composed of a main window 12 and a minimap window 14. The minimap window 14 is located at a corner of the main window 12 and is configured to display the keyframe. The main window 12 is configured to display a part of the keyframe located within a bounding box. A rectangular box 16 exists on each keyframe displayed in the minimap window 14 to indicate a position of the monitored target in each keyframe. In this way, the region of real interest is zoomed in in the main window 12 while retaining an original image in the minimap window 14 to provide position information.

In the Picture-in-Picture mode, the display window 10 is composed of a main window 12 and a child window 18. The child window 18 is located at a corner of the main window 12. One of the main window 12 and the child window 18 is configured to display the monitoring video generated in real time, and the other is configured to display a primary video including the monitored target from a camera. Contents displayed in the main window 12 and the child window 18 are switched by clicking/tapping the child window 18. In this way, two different videos may be viewed simultaneously.

It should be understood that although the description is illustrated according to each aspect, each aspect does not necessarily include an independent technical solution. The illustration of the specification is merely for clarity. A person skilled in the art should consider the description as a whole, and the technical solutions in the aspects may be properly combined to form other implementations that a person skilled in the art can understand.

The series of detailed descriptions listed above are merely specific illustrations of the feasible aspects of the present disclosure, and are not intended to limit the protection scope of the present disclosure. Any equivalent implementations or changes made without departing from the spirit of the present disclosure, such as the combination, segmentation, or repetition of features, should be included in the protection scope of the present disclosure.

The invention claimed is:

1. A monitoring video generation method, applicable to a computer tomography (CT) machine, wherein a monitored target is located on a patient table of the CT machine, and the patient table of the CT machine is movable relative to a gantry of the CT machine in an extending direction, the monitoring video generation method comprising:

acquiring a plurality of primary videos comprising the monitored target, wherein fields of view of the plurality of primary videos are fixed relative to a position of the gantry of the CT machine;

determining a keyframe according to a region in an initial frame of each of the primary videos surrounding the monitored target, and determining a bounding box surrounding the monitored target in the keyframe;

determining, for each of the primary videos, the bounding box surrounding the monitored target in each subsequent frame by using an automatic detection algorithm, a coordinate conversion algorithm, or an optical flow method, wherein the step of determining the bounding box by using the coordinate conversion algorithm specifically comprises:

mapping, through the coordinate conversion algorithm, coordinates of a bounding box in a keyframe at a previous frame moment to a coordinate system where the gantry of the CT machine is located;

calculating, according to a physical movement vector of the patient table of the CT machine relative to the gantry of the CT machine between two frames, a position of the bounding box in a frame at a next frame moment of the same primary video in the coordinate system where the gantry of the CT machine is located;

then mapping the coordinates to the frame at the next frame moment of each of the primary videos according to coordinate correspondences between cameras that acquire the primary videos and between the cameras and the gantry; and determining the bounding box surrounding the monitored target after coordinate update in the frame at the next frame moment of each of the primary videos; and selecting, for each frame moment from the frames of the plurality of primary videos, a frame in which the region of the monitored target within the bounding box has a largest area as the keyframe, and generating a monitoring video in real time according to a part of each selected keyframe located within the bounding box.

2. The monitoring video generation method according to claim 1, wherein the step of determining the keyframe according to the region in the initial frame of each of the primary videos surrounding the monitored target specifically comprises:

determining the region in the initial frame of each of the primary videos surrounding the monitored target through the automatic detection algorithm or manual selection; and selecting a frame in the initial frames in which the region surrounding the monitored target has the largest area as the keyframe.

3. A monitoring video generation method, applicable to a computer tomography (CT) machine, wherein a monitored target is located on a patient table of the CT machine, and the patient table of the CT machine is movable relative to a gantry of the CT machine in an extending direction, the monitoring video generation method comprising:

acquiring a plurality of primary videos comprising the monitored target, wherein fields of view of the plurality of primary videos are fixed relative to a position of the gantry of the CT machine;

determining a keyframe according to a region in an initial frame of each of the primary videos surrounding the monitored target, and determining a bounding box surrounding the monitored target in the keyframe;

determining, for each of the primary videos, the bounding box surrounding the monitored target in each subsequent frame by using an automatic detection algorithm, a coordinate conversion algorithm, or an optical flow method, wherein the step of determining the bounding box by using the optical flow method specifically comprises:

calculating coordinates of the bounding box in a frame at a next frame moment of the same primary video through the optical flow method by using coordinates of the bounding box in the keyframe at a previous frame moment as a reference;

then mapping, through coordinate conversion, the calculated coordinates of the bounding box in the frame at the next frame moment to a coordinate system where the gantry of the CT machine is located;

mapping the coordinates to a frame at a next frame moment of each of the primary videos according to coordinate correspondences between cameras that acquire the primary videos and between the cameras and the gantry; and determining the bounding box surrounding the monitored target after coordinate update in the frame at the next frame moment of each of the primary videos; and selecting, for each frame moment from the frames of the plurality of primary videos, a frame in which the region of the monitored target within the bounding box has a largest area as the keyframe, and generating a monitoring video in real time according to a part of each selected keyframe located within the bounding box.

4. A monitoring video generation system, comprising a non-transitory computer-readable storage medium and a processor, wherein the non-transitory computer-readable storage medium stores code, and when the processor executes the code, the monitoring video generation system performs the monitoring video generation method according to claim 1.

5. The monitoring video generation system according to claim 4, further comprising:

a display having a display window configured to display the monitoring video generated in real time, wherein the monitoring video is generated in real time in a minimap mode or a Picture-in-Picture mode.

6. The monitoring video generation system according to claim 5, wherein in the minimap mode, the display window is composed of a main window and a minimap window, the minimap window is configured to display the keyframe at each frame moment, the main window is configured to display a part of each keyframe located within the bounding box, and a rectangular box exists on each keyframe displayed in the minimap window to indicate a position of the monitored target in each keyframe.

7. The monitoring video generation system according to claim 5, wherein the display window in the Picture-in-Picture mode is composed of a main window and a child window, one of the main window and the child window is configured to display the monitoring video generated in real time, the other is configured to display a primary video comprising the monitored target from a camera, and content displayed in the main window and the child window are switched by clicking/tapping the child window.

* * * * *